(12) United States Patent
Copeland et al.

(10) Patent No.: US 10,631,986 B2
(45) Date of Patent: Apr. 28, 2020

(54) TRANSCATHETER DELIVERY SYSTEM WITH TRANSVERSE WHEEL ACTUATION

(71) Applicant: St. Jude Medical, Cardiology Division, Inc., St. Paul, MN (US)

(72) Inventors: David John Copeland, Minnetonka, MN (US); Travis Michael Beckerle, St. Paul, MN (US); Joseph Gordon, Mansfield, MA (US); Bruce Edward Frohman, Saint Louis Park, MN (US); Michael William Metz, Minneapolis, MN (US); Savannah Grace Kyle, Minneapolis, MN (US); Kelsey Hill, Minneapolis, MN (US); Michael Shane Morrissey, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 230 days.

(21) Appl. No.: 15/827,401

(22) Filed: Nov. 30, 2017

(65) Prior Publication Data

US 2018/0153693 A1 Jun. 7, 2018

Related U.S. Application Data

(60) Provisional application No. 62/429,315, filed on Dec. 2, 2016.

(51) Int. Cl.
*A61F 2/24* (2006.01)
*A61F 2/966* (2013.01)
(Continued)

(52) U.S. Cl.
CPC .......... *A61F 2/2436* (2013.01); *A61F 2/2427* (2013.01); *A61F 2/966* (2013.01);
(Continued)

(58) Field of Classification Search
CPC ...... A61F 2/2436; A61F 2/2427; A61F 2/966; A61F 2002/9522; A61F 2002/9517;
(Continued)

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| AU | 2011202175 B1 | 7/2011 |
| DE | 19857887 A1 | 7/2000 |

(Continued)

OTHER PUBLICATIONS

International Search Report from PCT/US2017/063893, dated Feb. 7, 2018, 3 pages.

(Continued)

*Primary Examiner* — Julian W Woo
(74) *Attorney, Agent, or Firm* — Lerner, David, Littenberg, Krumholz & Mentlik, LLP (57) ABSTRACT

A delivery device for a collapsible prosthetic heart valve, the delivery device including an inner shaft, a distal sheath disposed about a portion of the inner shaft and forming a compartment with the inner shaft, the compartment adapted to receive the valve, the inner shaft and the distal sheath being movable relative to one another, and a handle including a frame having a longitudinal axis, a proximal end and a distal end, the handle including a deployment actuator and a hub, the deployment actuator and the hub being independently capable of opening and closing the compartment, a resheathing lock configured to alert a user of a position of the distal sheath and to impede movement of the distal sheath, and an indicator disposed on the frame and capable of showing an extent of deployment of the valve.

17 Claims, 8 Drawing Sheets

(51) Int. Cl.
  *A61F 2/95* (2013.01)
  *A61M 25/00* (2006.01)
  *A61B 17/00* (2006.01)

(52) U.S. Cl.
  CPC ............ *A61B 17/00234* (2013.01); *A61B 2017/00243* (2013.01); *A61B 2017/00292* (2013.01); *A61F 2/2418* (2013.01); *A61F 2002/9517* (2013.01); *A61F 2002/9522* (2013.01); *A61F 2002/9534* (2013.01); *A61F 2250/0097* (2013.01); *A61M 2025/0008* (2013.01)

(58) Field of Classification Search
  CPC ...... A61F 2250/0097; A61F 2002/9534; A61F 2/2418; A61B 2017/00292; A61B 2017/0024; A61B 17/00234; A61M 2025/0008
  See application file for complete search history.

(56) References Cited

U.S. PATENT DOCUMENTS

| | | | |
|---|---|---|---|
| 4,423,730 A | | 1/1984 | Gabbay |
| 4,491,986 A | | 1/1985 | Gabbay |
| 4,759,758 A | | 7/1988 | Gabbay |
| 4,922,905 A | | 5/1990 | Strecker |
| 5,391,172 A | | 2/1995 | Williams et al. |
| 5,411,552 A | | 5/1995 | Andersen et al. |
| 5,456,667 A | | 10/1995 | Ham et al. |
| 5,480,423 A | | 1/1996 | Ravenscroft et al. |
| 5,707,376 A | * | 1/1998 | Kavteladze ............... A61F 2/90 623/1.11 |
| 5,843,167 A | | 12/1998 | Dwyer et al. |
| 5,924,424 A | | 7/1999 | Stevens et al. |
| 5,935,163 A | | 8/1999 | Gabbay |
| 5,961,549 A | | 10/1999 | Nguyen et al. |
| 5,968,068 A | | 10/1999 | Dehdashtian et al. |
| 6,077,297 A | | 6/2000 | Robinson et al. |
| 6,083,257 A | | 7/2000 | Taylor et al. |
| 6,090,140 A | | 7/2000 | Gabbay |
| 6,214,036 B1 | | 4/2001 | Letendre et al. |
| 6,264,691 B1 | | 7/2001 | Gabbay |
| 6,267,783 B1 | | 7/2001 | Letendre et al. |
| 6,306,141 B1 | | 10/2001 | Jervis |
| 6,368,348 B1 | | 4/2002 | Gabbay |
| 6,419,695 B1 | | 7/2002 | Gabbay |
| 6,488,702 B1 | | 12/2002 | Besselink |
| 6,514,261 B1 | | 2/2003 | Randall et al. |
| 6,517,576 B2 | | 2/2003 | Gabbay |
| 6,533,810 B2 | | 3/2003 | Hankh et al. |
| 6,582,464 B2 | | 6/2003 | Gabbay |
| 6,610,088 B1 | | 8/2003 | Gabbay |
| 6,623,518 B2 | | 9/2003 | Thompson et al. |
| 6,685,625 B2 | | 2/2004 | Gabbay |
| 6,719,789 B2 | | 4/2004 | Cox |
| 6,730,118 B2 | | 5/2004 | Spenser et al. |
| 6,736,845 B2 | | 5/2004 | Marquez et al. |
| 6,783,556 B1 | | 8/2004 | Gabbay |
| 6,790,230 B2 | | 9/2004 | Beyersdorf et al. |
| 6,814,746 B2 | | 11/2004 | Thompson et al. |
| 6,830,584 B1 | | 12/2004 | Seguin |
| 6,866,669 B2 | * | 3/2005 | Buzzard ............... A61F 2/95 606/108 |
| 6,869,444 B2 | | 3/2005 | Gabbay |
| 6,893,460 B2 | | 5/2005 | Spenser et al. |
| 6,908,481 B2 | | 6/2005 | Cribier |
| 7,018,406 B2 | | 3/2006 | Seguin et al. |
| 7,025,780 B2 | | 4/2006 | Gabbay |
| 7,105,016 B2 | | 9/2006 | Shiu et al. |
| 7,137,184 B2 | | 11/2006 | Schreck |
| 7,160,322 B2 | | 1/2007 | Gabbay |
| 7,247,167 B2 | | 7/2007 | Gabbay |
| 7,267,686 B2 | | 9/2007 | DiMatteo et al. |
| 7,311,730 B2 | | 12/2007 | Gabbay |
| 7,326,236 B2 | | 2/2008 | Andreas et al. |
| 7,329,278 B2 | | 2/2008 | Seguin et al. |
| 7,374,573 B2 | | 5/2008 | Gabbay |
| 7,381,218 B2 | | 6/2008 | Schreck |
| 7,399,315 B2 | | 7/2008 | Iobbi |
| 7,419,501 B2 | | 9/2008 | Chiu et al. |
| 7,452,371 B2 | | 11/2008 | Pavcnik et al. |
| 7,476,244 B2 | | 1/2009 | Buzzard et al. |
| 7,510,572 B2 | | 3/2009 | Gabbay |
| RE40,816 E | | 6/2009 | Taylor et al. |
| 7,585,321 B2 | | 9/2009 | Cribier |
| 7,682,390 B2 | | 3/2010 | Seguin |
| 7,731,742 B2 | | 6/2010 | Schlick et al. |
| 7,803,185 B2 | | 9/2010 | Gabbay |
| 7,846,203 B2 | | 12/2010 | Cribier |
| 7,846,204 B2 | | 12/2010 | Letac et al. |
| 7,914,569 B2 | | 3/2011 | Nguyen et al. |
| 7,967,829 B2 | | 6/2011 | Gunderson et al. |
| 7,993,384 B2 | | 8/2011 | Wu |
| 8,043,353 B2 | | 10/2011 | Kaufmann et al. |
| D648,854 S | | 11/2011 | Braido |
| D652,926 S | | 1/2012 | Braido |
| D652,927 S | | 1/2012 | Braido et al. |
| D653,341 S | | 1/2012 | Braido et al. |
| D653,342 S | | 1/2012 | Braido et al. |
| D653,343 S | | 1/2012 | Ness et al. |
| D654,169 S | | 2/2012 | Braido |
| D654,170 S | | 2/2012 | Braido et al. |
| 8,353,955 B2 | | 1/2013 | Styrc et al. |
| 8,562,663 B2 | | 10/2013 | Mearns et al. |
| 8,568,475 B2 | | 10/2013 | Nguyen et al. |
| 8,778,019 B2 | * | 7/2014 | Knippel ............... A61F 2/2436 623/2.11 |
| 8,790,386 B2 | | 7/2014 | Dwork |
| 8,814,931 B2 | | 8/2014 | Wang et al. |
| 9,675,485 B2 | * | 6/2017 | Essinger ............... A61F 2/2418 |
| 9,820,877 B2 | * | 11/2017 | Cummins ............... A61F 2/966 |
| 9,867,701 B2 | * | 1/2018 | Morris .................. A61F 2/2436 |
| 9,883,960 B2 | * | 2/2018 | Cummins ............... A61F 2/962 |
| 9,974,376 B1 | * | 5/2018 | Liu ........................ A45D 40/00 |
| 10,064,748 B2 | * | 9/2018 | Shimoyama ........... A61F 2/852 |
| 10,213,299 B2 | * | 2/2019 | Backus .................. A61F 2/243 |
| 10,292,820 B2 | * | 5/2019 | Morrissey ............. A61F 2/2436 |
| 2002/0036220 A1 | | 3/2002 | Gabbay |
| 2002/0183827 A1 | | 12/2002 | Derus et al. |
| 2003/0050694 A1 | | 3/2003 | Yang et al. |
| 2003/0130726 A1 | | 7/2003 | Thorpe et al. |
| 2003/0144725 A1 | | 7/2003 | Lombardi |
| 2004/0039436 A1 | | 2/2004 | Spenser et al. |
| 2004/0049262 A1 | | 3/2004 | Obermiller et al. |
| 2004/0093075 A1 | | 5/2004 | Kuehne |
| 2004/0148009 A1 | | 7/2004 | Buzzard et al. |
| 2004/0186563 A1 | | 9/2004 | Lobbi |
| 2004/0210304 A1 | | 10/2004 | Seguin et al. |
| 2004/0260390 A1 | | 12/2004 | Sarac et al. |
| 2005/0004583 A1 | | 1/2005 | Oz et al. |
| 2005/0027305 A1 | | 2/2005 | Shiu et al. |
| 2005/0049667 A1 | | 3/2005 | Arbefeuille et al. |
| 2005/0080476 A1 | | 4/2005 | Gunderson et al. |
| 2005/0096726 A1 | | 5/2005 | Sequin et al. |
| 2005/0137695 A1 | | 6/2005 | Salahieh et al. |
| 2005/0137697 A1 | | 6/2005 | Salahieh et al. |
| 2005/0149159 A1 | | 7/2005 | Andreas et al. |
| 2005/0240254 A1 | | 10/2005 | Austin |
| 2005/0256566 A1 | | 11/2005 | Gabbay |
| 2006/0008497 A1 | | 1/2006 | Gabbay |
| 2006/0074484 A1 | | 4/2006 | Huber |
| 2006/0106415 A1 | | 5/2006 | Gabbay |
| 2006/0122692 A1 | | 6/2006 | Gilad et al. |
| 2006/0142848 A1 | | 6/2006 | Gabbay |
| 2006/0167468 A1 | | 7/2006 | Gabbay |
| 2006/0173532 A1 | | 8/2006 | Flagle et al. |
| 2006/0206202 A1 | | 9/2006 | Bonhoeffer et al. |
| 2006/0241744 A1 | | 10/2006 | Beith |
| 2006/0259120 A1 | | 11/2006 | Vongphakdy et al. |
| 2006/0259136 A1 | | 11/2006 | Nguyen et al. |
| 2006/0259137 A1 | | 11/2006 | Artof et al. |
| 2006/0265056 A1 | | 11/2006 | Nguyen et al. |
| 2006/0276813 A1 | | 12/2006 | Greenberg |

(56) References Cited

U.S. PATENT DOCUMENTS

| | | |
|---|---|---|
| 2006/0282150 A1 | 12/2006 | Olson et al. |
| 2006/0282157 A1 | 12/2006 | Hill et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0156225 A1 | 7/2007 | George et al. |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0260301 A1 | 11/2007 | Chuter et al. |
| 2007/0288087 A1 | 12/2007 | Fearnot et al. |
| 2008/0004688 A1 | 1/2008 | Spenser et al. |
| 2008/0009940 A1 | 1/2008 | Cribier |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082159 A1 | 4/2008 | Tseng et al. |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228264 A1 | 9/2008 | Li et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269878 A1 | 10/2008 | Iobbi |
| 2008/0269879 A1 | 10/2008 | Sathe et al. |
| 2009/0024137 A1 | 1/2009 | Chuter et al. |
| 2009/0054975 A1 | 2/2009 | del Nido et al. |
| 2009/0105798 A1 | 4/2009 | Koch |
| 2009/0112309 A1 | 4/2009 | Jaramillo et al. |
| 2009/0118826 A1 | 5/2009 | Khaghani |
| 2009/0138079 A1 | 5/2009 | Tuval et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 | 2/2010 | Alon et al. |
| 2010/0082094 A1 | 4/2010 | Quadri et al. |
| 2010/0087907 A1 | 4/2010 | Lattouf |
| 2010/0114305 A1 | 5/2010 | Kang et al. |
| 2010/0121434 A1 | 5/2010 | Paul et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0174290 A1 | 7/2010 | Wuebbeling et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0208298 A1 | 8/2011 | Tuval et al. |
| 2011/0224678 A1 | 9/2011 | Gabbay |
| 2011/0282425 A1 | 11/2011 | Dwork |
| 2011/0288626 A1 | 11/2011 | Straubinger et al. |
| 2011/0295216 A1 | 12/2011 | Miller |
| 2012/0022635 A1 | 1/2012 | Yamashita |
| 2012/0053574 A1 | 3/2012 | Murray, III et al. |
| 2012/0078352 A1 | 3/2012 | Wang et al. |
| 2012/0197391 A1 | 8/2012 | Alkhatib et al. |
| 2012/0310332 A1 | 12/2012 | Murray et al. |
| 2013/0030520 A1 | 1/2013 | Lee et al. |
| 2013/0138118 A1 | 5/2013 | Doyle |
| 2013/0231735 A1 | 9/2013 | Deem et al. |
| 2013/0297011 A1 | 11/2013 | Morris et al. |
| 2013/0304179 A1 | 11/2013 | Bialas et al. |
| 2014/0067050 A1 | 3/2014 | Costello et al. |
| 2014/0135909 A1 | 5/2014 | Carr et al. |
| 2014/0343670 A1 | 11/2014 | Bakis et al. |
| 2015/0305867 A1 | 10/2015 | Liu et al. |
| 2017/0056169 A1 | 3/2017 | Johnson et al. |

FOREIGN PATENT DOCUMENTS

| | | |
|---|---|---|
| DE | 20000659 U1 | 5/2001 |
| DE | 10121210 A1 | 11/2002 |
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| FR | 2847800 B1 | 10/2005 |
| JP | 2001504717 A | 4/2001 |
| JP | 2003334254 A | 11/2003 |
| JP | 2004130074 | 4/2004 |
| JP | 2010504820 A | 2/2010 |
| JP | 2010526609 A | 8/2010 |
| JP | 2010531193 | 9/2010 |
| JP | 2012500665 A | 1/2012 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0018330 A1 | 4/2000 |
| WO | 0069368 A2 | 11/2000 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 07071436 A2 | 6/2007 |
| WO | 2008042266 A2 | 4/2008 |
| WO | 08070797 A2 | 6/2008 |
| WO | 2008138584 A1 | 11/2008 |
| WO | 2009001309 | 12/2008 |
| WO | 2009011866 A1 | 1/2009 |
| WO | 2009029199 A1 | 3/2009 |
| WO | 2009042196 A2 | 4/2009 |
| WO | 2009091509 A1 | 7/2009 |
| WO | 2010008548 A2 | 1/2010 |
| WO | 2010008549 A1 | 1/2010 |
| WO | 2010051025 A1 | 5/2010 |
| WO | 2010087975 A1 | 8/2010 |
| WO | 2010096176 A1 | 8/2010 |
| WO | 2010098857 A1 | 9/2010 |
| WO | 2011137531 A9 | 11/2011 |
| WO | 2012026965 A2 | 3/2012 |
| WO | 2012036741 A2 | 3/2012 |
| WO | 2016059084 A2 | 4/2016 |

OTHER PUBLICATIONS

Alkhatib, U.S. Appl. No. 13/216,124, filed Aug. 23, 2011, titled "Leaflet Suturing to Commissure Points for Prosthetic Heart Valve".

(56) References Cited

OTHER PUBLICATIONS

Australian Examination Report for Application No. 2011293898 dated Jul. 26, 2013.
Extended European Search Report for Application No. 16196712 dated May 9, 2017.
International Search Report Application No. PCT/US2011/048963, dated Dec. 15, 2011.
International Search Report Application No. PCT/US2011/048967, dated Dec. 15, 2011.
International Search Report Application No. PCT/US2011/048989, dated Dec. 15, 2011.
International Search Report for Application No. PCT/US2011/001450 dated Mar. 5, 2012.
International Search Report for Application No. PCT/US2011/001597 dated Mar. 7, 2012.
International Search Report for Application No. PCT/US2011/001615 dated Jul. 11, 2012.
International Search Report for Application No. PCT/US2013/039407 dated Feb. 10, 2014.
International Search Report for Application No. PCT/US2014/064253 dated Feb. 3, 2015.
Japanese Office Action for Application No. 2013-525891 dated May 8, 2015.
Knippel, U.S. Appl. No. 13/234,782, filed Sep. 16, 2011, titled "Staged Deployment Devices and Method for Transcatheter Heart Valve Delivery".
Morris, U.S. Appl. No. 13/788,820, filed Mar. 7, 2013, titled "Devices and Methods for Transcatheter Heart Valve Delivery".
Ruiz, Carlos, Overview of PRE-CE Mark Transcatheter Aortic Valve Technologies, Euro PCR, dated May 25, 2010.
Wang, U.S. Appl. No. 13/212,442, filed Aug. 18, 2011, titled "Staged Deployment Devices and Methods for Transcatheter Heart Valve Delivery Systems".
International Search Report and Written Opinion for PCT/US2018/031973, dated Oct. 19, 2018.

\* cited by examiner

TRANSCATHETER DELIVERY SYSTEM WITH TRANSVERSE WHEEL ACTUATION

CROSS-REFERENCE TO RELATED APPLICATION

This application claims the benefit of the filing date of U.S. Provisional Patent Application No. 62/429,315, filed on Dec. 2, 2016, the disclosure of which is hereby incorporated herein by reference.

BACKGROUND OF THE INVENTION

The present disclosure relates to a delivery system for heart valve replacement and, in particular, for replacement of collapsible prosthetic heart valves. More particularly, the present disclosure relates to delivery systems for collapsible prosthetic heart valves that may be repositioned during the deployment procedure.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve so that the valve can be repositioned while in a collapsed state. After the valve has been repositioned, the user can again release the valve.

Once a self-expanding valve has been fully deployed, it expands to a diameter larger than that of the sheath that previously retained the valve in the collapsed condition, making resheathing difficult. In order for the user to be able to more readily resheathe a valve, it is preferable that the valve be only partially deployed, with a portion of the valve still collapsed inside of the sheath.

Despite the various improvements that have been made to the collapsible prosthetic heart valve delivery process, conventional delivery devices, systems, and methods suffer from some shortcomings. For example, in some delivery devices for self-expanding valves, it is difficult to control how much of the valve remains in the sheath during a partial deployment, and the user may accidentally deploy the valve fully before verifying that the annulus end of the valve is in the optimal position in the patient's valve annulus, thereby taking away the opportunity to resheathe and reposition the valve. Moreover, it is difficult during prosthetic heart valve delivery to determine whether a valve assembly will function as intended without full deployment of the heart valve. Due to anatomical variations between patients, a fully deployed heart valve may need to be removed from the patient if it appears that the valve is not functioning properly. Removing a fully deployed heart valve increases the length of the procedure and increases the risk of infection and/or damage to heart tissue.

There therefore is a need for further improvements to the devices, systems, and methods for transcatheter delivery of collapsible prosthetic heart valves, and in particular, self-expanding prosthetic heart valves. Among other advantages, the present disclosure may address one or more of these needs.

SUMMARY OF THE INVENTION

In some embodiments, a delivery device for a collapsible prosthetic heart valve, the delivery device includes an inner shaft, a distal sheath disposed about a portion of the inner shaft and forming a compartment with the inner shaft, the compartment being adapted to receive the prosthetic heart valve, the inner shaft and the distal sheath being movable relative to one another, and a handle including a frame having a longitudinal axis, a proximal end and a distal end, the handle further including a deployment actuator and a hub, each of the deployment actuator and the hub being independently capable of opening and closing the compartment, a resheathing lock configured to alert a user of a position of the distal sheath and to impede movement of the distal sheath, and an indicator disposed on the frame and capable of showing an extent of deployment of the prosthetic heart valve.

In some embodiments, a delivery device for a collapsible prosthetic heart valve, the delivery device includes an inner shaft, a distal sheath disposed about a portion of the inner shaft and forming a compartment with the inner shaft, the compartment being adapted to receive the prosthetic heart valve, the inner shaft and the distal sheath being movable relative to one another, and a handle including a frame having a longitudinal axis, a proximal end and a distal end, the handle further including a deployment actuator and a hub, each of the deployment actuator and the hub being independently capable of opening and closing the compartment.

In some embodiments, a delivery device for a collapsible prosthetic heart valve, the delivery device includes an inner shaft, a distal sheath disposed about a portion of the inner shaft and forming a compartment with the inner shaft, the compartment being adapted to receive the prosthetic heart valve, the inner shaft and the distal sheath being movable relative to one another, and a handle including a frame having a longitudinal axis, a proximal end and a distal end, the handle further including a visual indicator disposed on the frame and capable of showing an extent of deployment of the prosthetic heart valve.

BRIEF DESCRIPTION OF THE DRAWINGS

Various embodiments of the present delivery system are disclosed herein with reference to the drawings, wherein.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

As used herein in connection with prosthetic heart valves, the term "proximal" refers to the end of the heart valve closest to the heart when the heart valve is implanted in a patient, whereas the term "distal" refers to the end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user.

Figure 1:
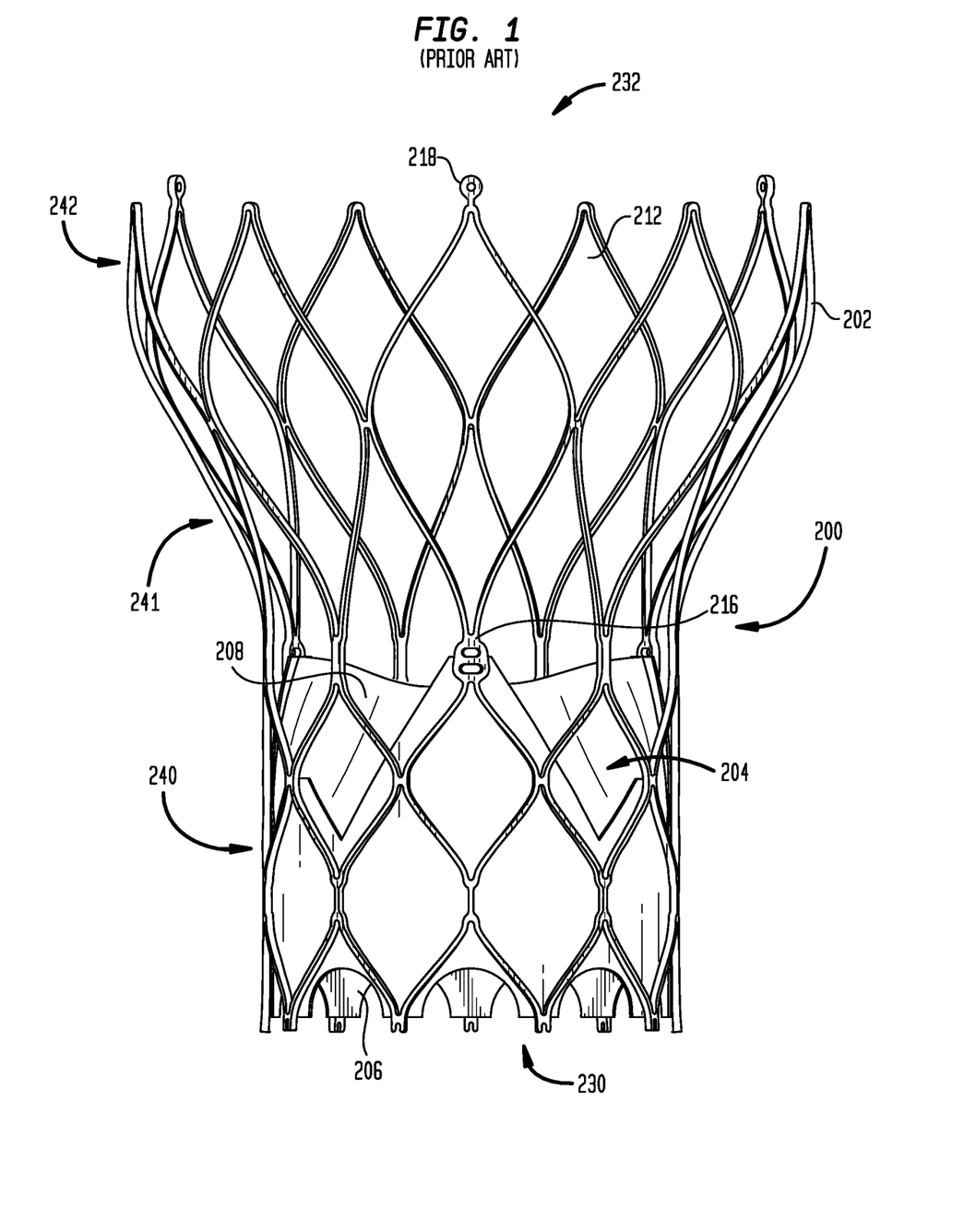
FIG. 1 is a side elevational view of a prior art collapsible prosthetic heart valve, showing the valve assembly attached to the stent.

FIG. 1 shows a collapsible prosthetic heart valve 200 according to the prior art. The prosthetic heart valve 200 is designed to replace the function of a native aortic valve of a patient. Examples of collapsible prosthetic heart valves are described in International Patent Application Publication No. WO/2009/042196; and U.S. Pat. Nos. 7,018,406 and 7,329,278, the disclosures of all of which are hereby incorporated herein by reference. As discussed in detail below, the prosthetic heart valve has an expanded condition and a collapsed condition. Although the delivery system is described herein in connection with its use to deliver a prosthetic heart valve for replacing a native aortic valve, the delivery system is not so limited, and may be used to deliver prosthetic valves for replacing other types of native or prosthetic cardiac valves.

Prosthetic heart valve 200 includes an expandable stent 202 which may be formed from any biocompatible material, such as metals, synthetic polymers or biopolymers capable of functioning as a stent. Stent 202 extends from a proximal or annulus end 230 to a distal or aortic end 232, and includes an annulus section 240 adjacent the proximal end and an aortic section 242 adjacent the distal end. The annulus section 240 has a relatively small cross-section in the expanded condition, while the aortic section 242 has a relatively large cross-section in the expanded condition. Preferably, annulus section 240 is in the form of a cylinder having a substantially constant diameter along its length. A transition section 241 may taper outwardly from the annulus section 240 to the aortic section 242. Each of the sections of the stent 202 includes a plurality of cells 212 connected to one another in one or more annular rows around the stent. For example, as shown in FIG. 1, the annulus section 240 may have two annular rows of complete cells 212 and the aortic section 242 and transition section 241 may each have one or more annular rows of partial cells 212. The cells 212 in the aortic section 242 may be larger than the cells 212 in the annulus section 240. The larger cells in the aortic section 242 better enable the prosthetic valve 200 to be positioned without the stent structure interfering with blood flow to the coronary arteries.

Stent 202 may include one or more retaining elements 218 at the distal end 232 thereof, the retaining elements being sized and shaped to cooperate with female retaining structures provided on the deployment device. The engagement of retaining elements 218 with the female retaining structures on the deployment device helps maintain prosthetic heart valve 200 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The prosthetic heart valve 200 includes a valve assembly 204 positioned in the annulus section 240. Valve assembly 204 includes a cuff 206 and a plurality of leaflets 208 which collectively function as a one-way valve. The commissure between adjacent leaflets 208 may be connected to commissure features 216 on stent 202. FIG. 1 illustrates a prosthetic heart valve for replacing a native tricuspid valve, such as the aortic valve. Accordingly, prosthetic heart valve 200 is shown in FIG. 1 with three leaflets 208, as well as three commissure features 216. As can be seen in FIG. 1, the commissure features 216 may lie at the intersection of four cells 212, two of the cells being adjacent one another in the same annular row, and the other two cells being in different annular rows and lying in end-to-end relationship. Preferably, commissure features 216 are positioned entirely within annulus section 240 or at the juncture of annulus section 240 and transition section 241. Commissure features 216 may include one or more eyelets which facilitate the suturing of the leaflet commissure to the stent. However, it will be appreciated that the prosthetic heart valves may have a greater or lesser number of leaflets and commissure features. Additionally, although cuff 206 is shown in FIG. 1 as being disposed on the luminal surface of annulus section 240, it is contemplated that the cuff may be disposed on the abluminal surface of annulus section 240, or may cover all or part of either or both of the luminal and abluminal surfaces of annulus section 240. Both the cuff 206 and the leaflets 208 may be wholly or partly formed of any suitable biological material or polymer.

In operation, a prosthetic heart valve, including the prosthetic heart valve described above, may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical or transseptal approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

In a prosthetic heart valve, the valve assembly may be spaced from the distal or aortic end of the stent by a distance that enables deployment of the heart valve by an amount sufficient for the valve leaflets of the prosthetic valve to operate as intended, while the distal end of the stent remains captured by the delivery device. More particularly, as will be explained further below, the annulus end of the prosthetic heart valve may be deployed first, while the aortic end of the prosthetic heart valve remains at least partially covered by a distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly. If the user determines that the positioning and operation of the valve are acceptable, the remainder of the valve may be deployed. However, if it is determined that the leaflet position is improper or that the valve is not functioning properly, the user may resheathe the valve and either reposition it for redeployment, or remove it entirely from the patient. This can be particularly important in very high risk patients who would typically be recipients of these types of valves, because of the nature of their condition and the impact that may have on the shape and/or condition of the native valve and valve annulus.

As is shown in FIG. 1, in one embodiment the entirety of valve assembly 204, including the leaflet commissures, is positioned in the annulus section 240 of stent 202. When opened, the leaflets may extend further into the transition section 241 or may be designed such that they remain substantially completely within the annulus section. That is, substantially the entirety of valve assembly 204 is positioned between the proximal end 230 of stent 202 and the commissure features 216, and none of the valve assembly 204 is positioned between commissure features 216 and the distal end 232 of the stent. Indeed, in some embodiments, the valve can be designed such that, upon partial deployment, the commissure features are fully exposed, oriented generally parallel to the direction of blood flow, and at or near their actual radially expanded position (but not necessarily their eventual position relative to the annulus), such that the leaflets can operate substantially as they would when the valve is fully deployed, even though enough of the stent is still retained within the delivery device or sheath to permit resheathing.

In a preferred arrangement, the distance between commissure features 216 and the distal end 232 of stent 202 will be about two-thirds of the length of the stent from the proximal end 230 to the distal end. This structural arrangement provides advantages in the deployment of prosthetic valve 200 as will be discussed in more detail with reference to FIGS. 2A and 2B. By having the entirety of valve assembly 204 positioned within annulus section 240, and by having a sufficient distance between commissure features 216 and the distal end 232 of stent 202, the valve assembly and commissures will not impede blood flow into the coronary arteries and will not interfere with access thereto during cardiac intervention, such as angiography, annuloplasty or stent placement.

Further, it is possible to partially deploy prosthetic valve 200 so that the valve assembly 204 thereof is able to fully function in its intended position in the native valve annulus, while a sufficient amount of the aortic section 242 is retained within the delivery device should resheathing become necessary. In other words, as will be explained in more detail below, the user may withdraw the distal sheath of the delivery device to gradually expose prosthetic valve 200, beginning at the proximal end 230. Continued withdrawal of the distal sheath will expose a greater extent of the prosthetic valve until the entire annulus section 240 and valve assembly 204 have been exposed. Upon exposure, these portions of the prosthetic valve will expand into engagement with the native valve annulus, entrapping the native valves, except for a small portion immediately adjacent the free end of the distal sheath which will be constrained by the distal sheath from fully expanding.

However, once the distal sheath has been withdrawn to expose a sufficient portion of the aortic section 242, the annulus section 240 will be able to fully expand and valve assembly 204 will be able to function in the same manner as if the entirety of prosthetic valve 200 had been deployed. At this juncture, it will be possible for the user to ascertain whether annulus section 240 and valve assembly 204 have been properly positioned relative to the native valve annulus, and whether the valve assembly is functioning properly. If the position and operation of valve assembly 204 are acceptable, the distal sheath may be withdrawn further to deploy the remainder of prosthetic valve 200. On the other hand, if the positioning or operation of valve assembly 204 are unacceptable, the user may advance the distal sheath to resheathe the prosthetic valve, reposition the valve and initiate the deployment procedure anew. And if it is determined that the valve is not functioning properly, it can be withdrawn from the patient and a new valve introduced.

Figure 2A:
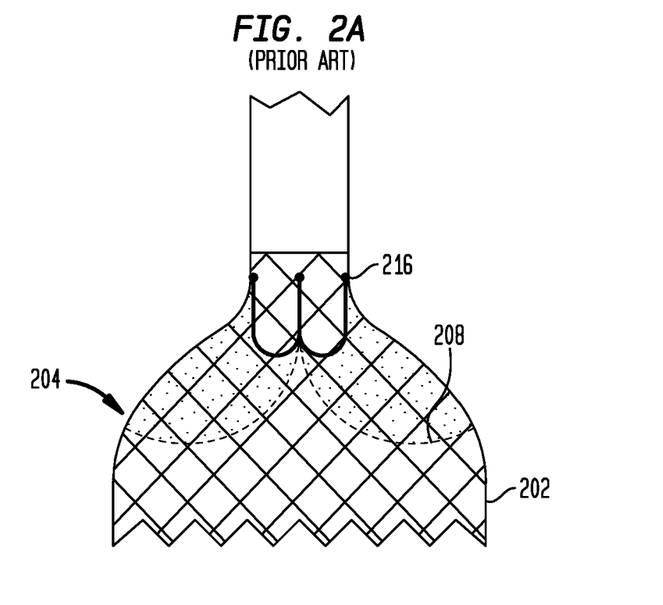
FIG. 2A is a highly schematic side elevational view showing partial deployment of a collapsible prosthetic heart valve with high placement according to the prior art.
Figure 2B:
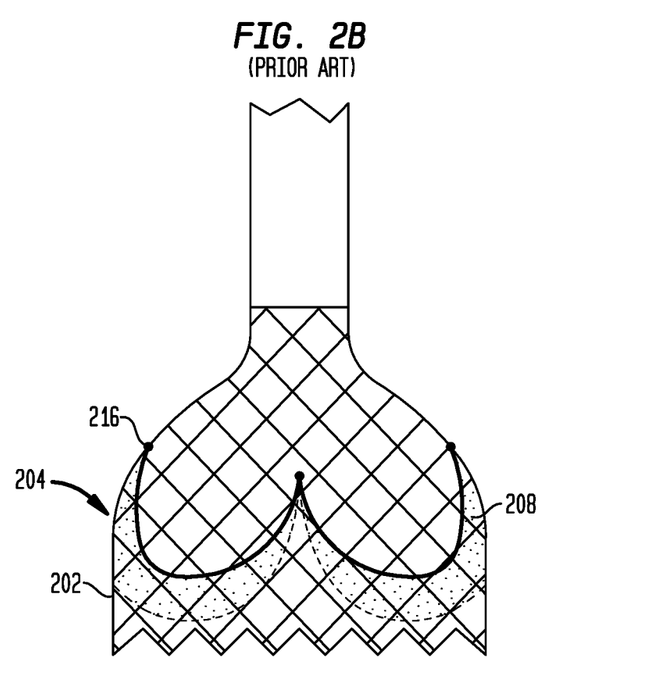
FIG. 2B is a highly schematic side elevational view showing partial deployment of a collapsible prosthetic heart valve with low placement according to the prior art.

It will be appreciated from the foregoing that the placement of the leaflets 208 within the stent 202 can affect the valve functioning during partial deployment. FIG. 2A illustrates a valve assembly 204 with high placement, while FIG. 2B illustrates a valve assembly with low placement. As used herein, the phrase "high placement" of a valve assembly refers to locating the valve assembly within the transition section 241 of the stent 202, or within the portion of the annulus section 240 closest to the transition section. The phrase "low placement" of a valve assembly refers to locating the valve assembly closer to the proximal end 230 of the stent 202 and entirely within the annulus section 240 thereof, such that the leaflets 208 are substantially disposed within the annulus section 208.

As seen in FIG. 2A, during partial deployment the annulus end of the heart valve 200 is unsheathed and allowed to expand. The distal end 232, including the aortic section 242, remains partially sheathed and coupled to the delivery device. Operation of the delivery device is described below in more detail with reference to FIGS. 3A-7B. Turning back to FIG. 2A, it will be appreciated that high placement of valve assembly 204 will cause the valve assembly to not be fully deployed when heart valve 200 is only partially deployed, thereby affecting leaflet function. Specifically, since the commissure features 216 are located closer to or within the transition section 241, they do not reach their fully expanded positions. As such, the leaflets 208 remain partially closed at this stage of deployment. Because of the location of the commissure features 216 and the leaflets 208, the valve assembly 204 cannot be tested during partial deployment. Instead, the user must unsheathe a portion of the aortic section 242 as well, which may pose problems if the valve assembly 204 is to be resheathed and redeployed.

In contrast to the prosthetic heart valve of FIG. 2A, the heart valve 200 of FIG. 2B exhibits low placement of the valve assembly 204 within the annulus section 240. Low placement of the valve assembly 204 enables the valve assembly to fully deploy when heart valve 200 is only partially deployed. As such, leaflets 208 reach their fully expanded and open positions during partial deployment and are able to function near normally, enabling a better assessment of the valve's functioning and final placement within the actual anatomy. Thus, if it appears that the valve needs to be moved, the heart valve 200 may be easily resheathed and repositioned. This concept is beneficial when dealing with less than ideal anatomical configurations.

The shape of the stent 202 during partial deployment will also affect the valve 204. If the stent shape is such that, while still partially retained by the sheath, it cannot open sufficiently to allow operation of the valve, it may not be possible to fully assess the operation of the valve in its intended placement position. Moreover, the height of the valve commissure features 216 relative to the proximal end 230 of the valve will affect the valve function. The lower the commissure features 216, meaning the closer to the proximal end 230, the more they will expand outwardly and the valve leaflets will be able to open during partial deployment, creating a flow passageway through the leaflets which approaches that of a fully deployed valve.

A transfemoral or transapical delivery device may be used to partially deploy the prosthetic heart valve such that an assessment may be made regarding flow through the valve and adequacy of coaptation. If, after the annulus section is unsheathed and the valve is tested, it is found that the valve needs to be repositioned, the annulus section may be resheathed and the valve redeployed as necessary.

Turning now to FIGS. 3A-D, an exemplary transfemoral delivery device 1010 for a collapsible prosthetic heart valve (or other types of self-expanding collapsible stents) has a catheter assembly 1016 for delivering the heart valve to and deploying the heart valve at a target location, and an operating handle 1020 for controlling deployment of the valve from the catheter assembly. The delivery device 1010 extends from a proximal end 1012 to a distal tip 1014. The catheter assembly 1016 is adapted to receive a collapsible prosthetic heart valve (not shown) in a compartment 1023 defined around an inner shaft 1026 and covered by a distal sheath 1024. The inner shaft 1026 extends through the operating handle 1020 to the distal tip 1014 of the delivery device, and includes a retainer 1025 affixed thereto at a spaced distance from distal tip 1014 and adapted to hold a collapsible prosthetic valve in the compartment 1023.

The distal sheath 1024 surrounds the inner shaft 1026 and is slidable relative to the inner shaft such that it can selectively cover or uncover the compartment 1023. The distal sheath 1024 is affixed at its proximal end to an outer shaft 1022, the proximal end of which is connected to the operating handle 1020 in a manner to be described. The distal end 1027 of the distal sheath 1024 abuts the distal tip 1014 when the distal sheath fully covers the compartment 1023, and is spaced apart from the distal tip 1014 when the compartment 1023 is at least partially uncovered.

The operating handle 1020 is adapted to control deployment of a prosthetic valve located in the compartment 1023 by permitting a user to selectively slide the outer shaft 1022 proximally or distally relative to the inner shaft 1026, or to slide the inner shaft 1026 relative to the outer shaft 1022, thereby respectively uncovering or covering the compartment with the distal sheath 1024. Operating handle 1020 includes frame 1030 which extends from a proximal end 1031 to a distal end and includes a top frame portion 1030a and a bottom frame portion 1030b. The proximal end of the inner shaft 1026 is coupled to a hub 1100, and the proximal end of the outer shaft 1022 is affixed to a carriage assembly 1040 (FIG. 4) that is slidable within the operating handle along a longitudinal axis of the frame 1030, such that a user can selectively slide the outer shaft relative to the inner shaft by sliding the carriage assembly relative to the frame. Alternatively, inner shaft 1026 may be actuated via hub 1100 to cover or uncover the compartment as will be discussed in greater detail below.

Figure 5A:
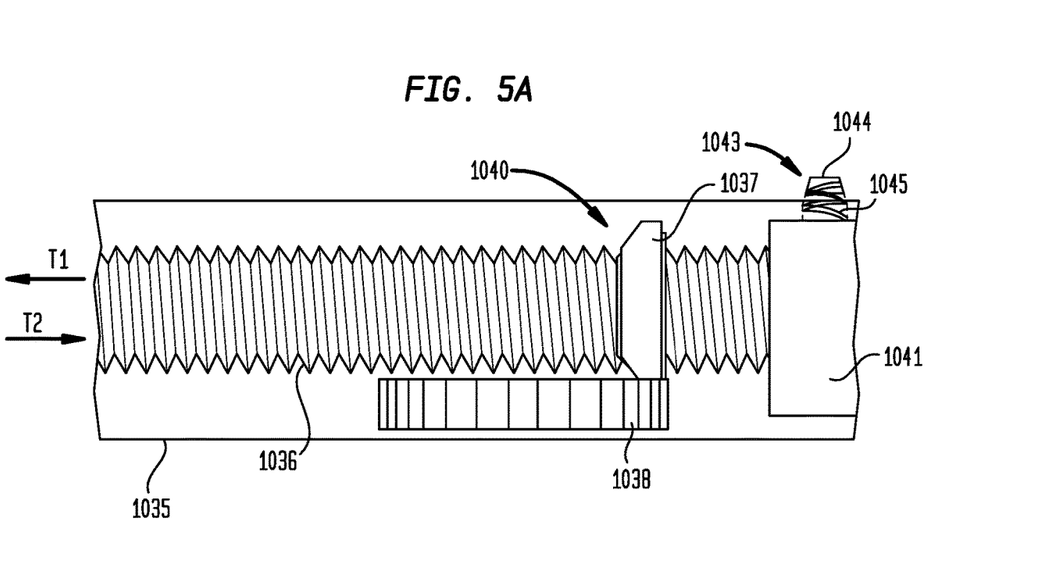
FIGS. 5A and 5B are enlarged schematic representations of a portion of the threaded rod of the carriage assembly of the operating handle and a pair of exemplary gears for use within the carriage assembly.
Figure 5B:
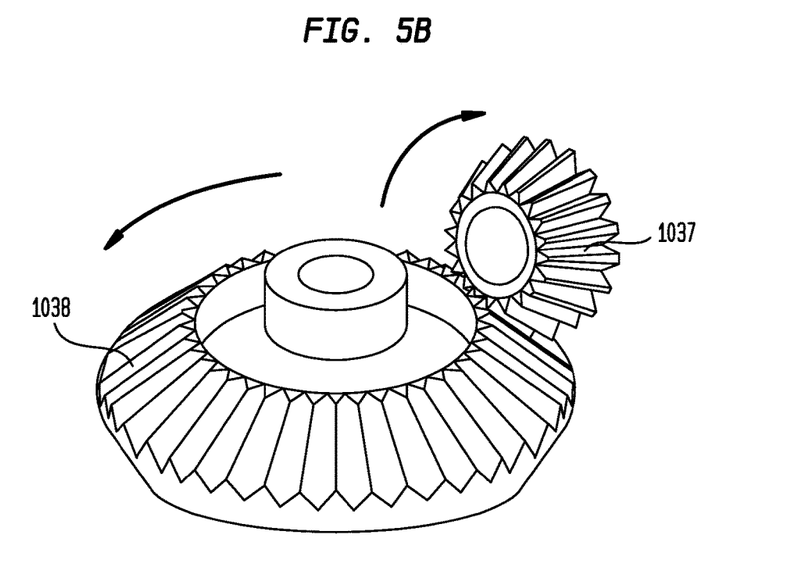
Figure 6:
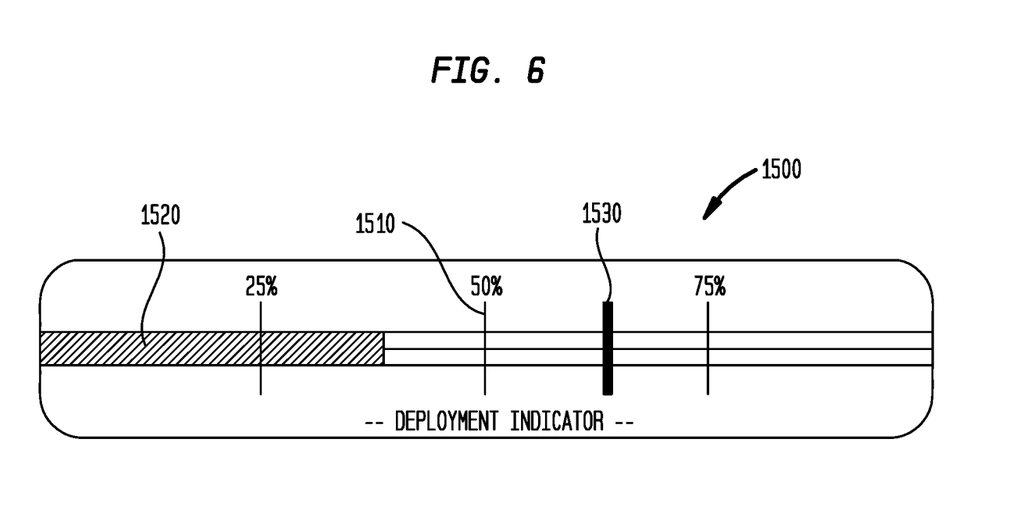
FIG. 6 shows a deployment indicator for use with the operating handle.

A first mechanism for covering and uncovering the compartment 1023 will be referred to as a "fine" technique as covering and uncovering occurs slowly with a high degree of precision. To allow for this technique, frame 1030 defines an elongated space 1035 in which carriage assembly 1040 may travel (FIG. 5A). The elongated space preferably permits the carriage assembly 1040 to travel a distance that is at least as long as the anticipated length of the prosthetic valve to be delivered (e.g., at least about 50 mm), such that the distal sheath 1024 can be fully retracted off of the prosthetic valve.

Figure 4:
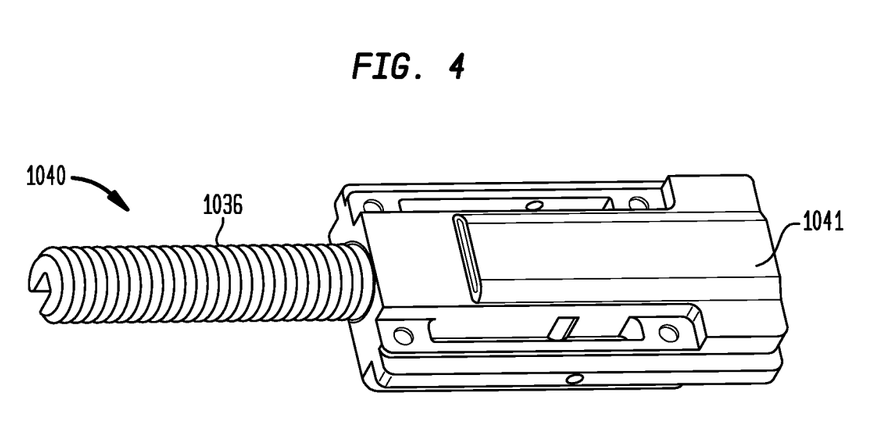
FIG. 4 is an enlarged perspective view of the carriage assembly of the handle of FIG. 3A.

The carriage assembly 1040 includes a main body 1041 and a threaded rod 1036 extending proximally therefrom along the longitudinal axis of the frame 1030. The threaded rod 1036 preferably is longer than the anticipated maximum travel distance of the carriage assembly 1040 within the elongated space 1035 (e.g., at least about 50 mm), such that the threaded rod does not fully withdraw from the elongated space 1035 during deployment of the prosthetic valve.

A deployment actuator 1021, shown in FIGS. 3A-D as a transverse wheel protruding from the lateral sides of frame 1030 is fixedly coupled to a first gear 1038 so that rotation of actuator 1021 causes a corresponding rotation of gear 1038. Gear 1038, in turn, is meshed with a second gear 1037 that is threadedly engaged on the threaded rod 1036. Gears 1037,1038 cooperate to convert rotation of deployment actuator 1021 into longitudinal translation of threaded rod 1036 in the direction of arrows T1 and T2 and a corresponding translation of main body 1041. Hence, rotation of actuator 1021 in one direction (either clockwise or counter-clockwise depending on the orientation of the threads on the threaded rod 1036) causes the carriage assembly 1040 to translate proximally within the elongated space 1035. Alternatively, actuator 1021 and first gear 1038 may be integral.

Figure 7A:
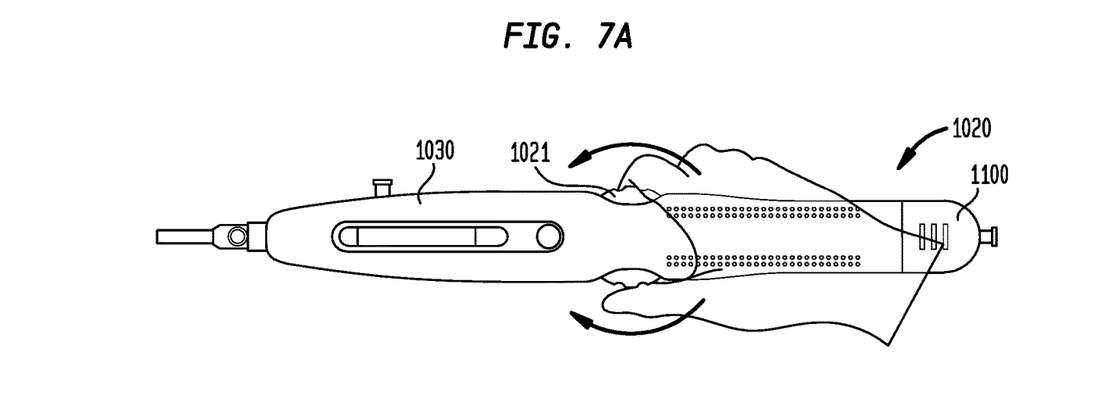
FIGS. 7A-B are schematic illustrations showing the use of the operating handle.
Figure 7B:
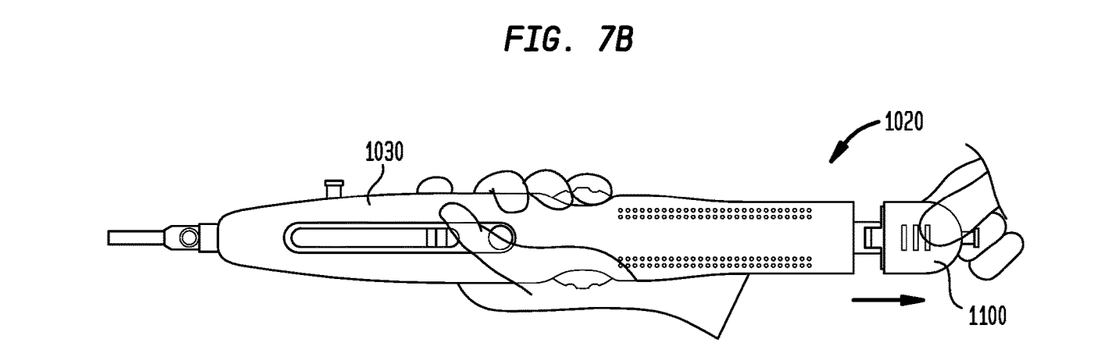

As outer shaft 1022 is fixedly connected to carriage assembly 1040, translation of the carriage assembly results in a longitudinal translation of outer shaft 1022 and with it distal sheath 1024. Thus, deployment actuator 1021 is configured to provide for fine movement of outer shaft 1022 for deployment and recapture of the prosthetic heart valve. As deployment actuator 1021 protrudes from the lateral sides of frame 1030 approximately halfway between the proximal and distal ends of the handle 1020, a user may readily rotate the actuator with his or her thumb and/or index finger (FIG. 7A).

Figure 3A:
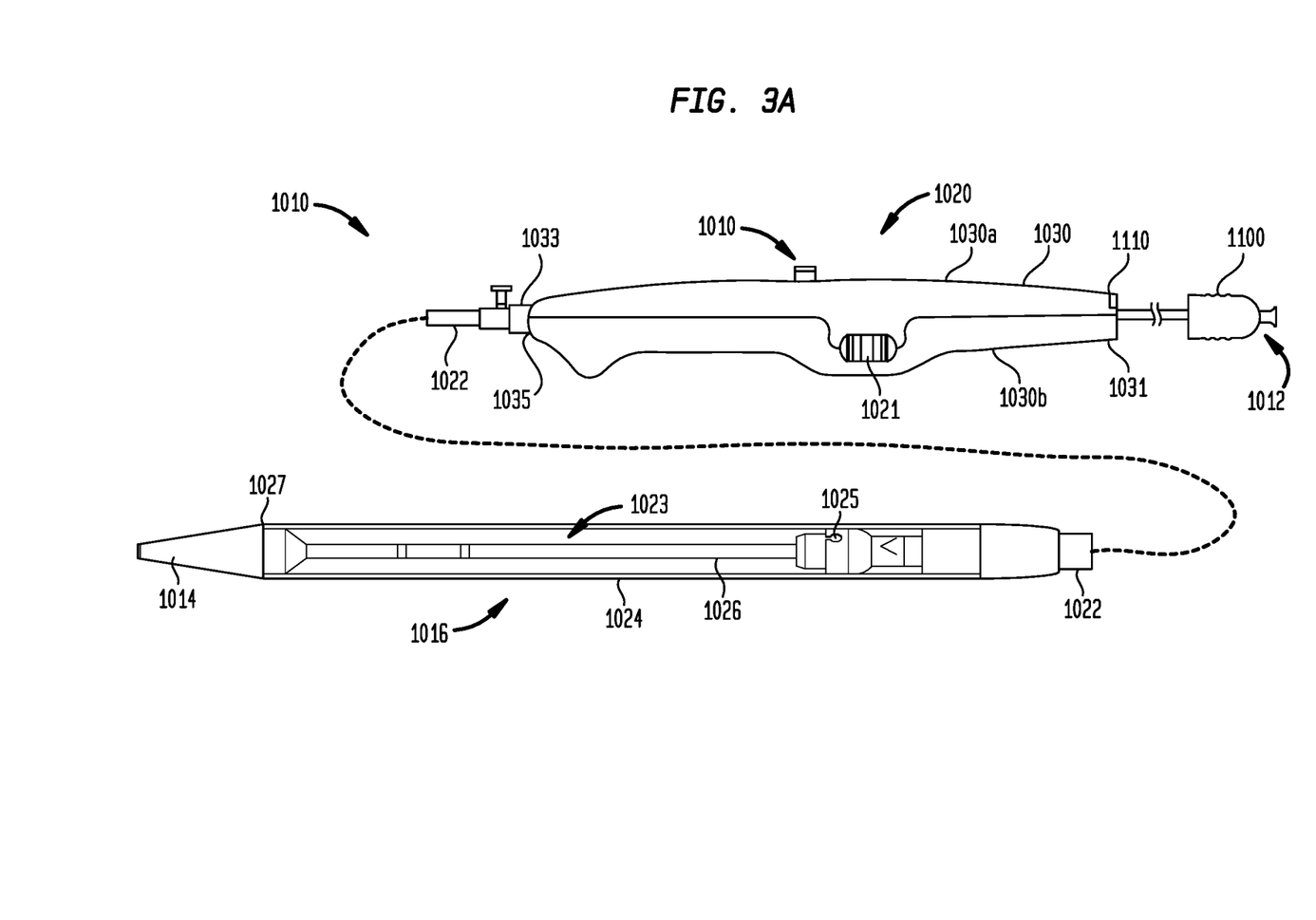
FIG. 3A is side view of an operating handle for a transfemoral delivery device for a collapsible prosthetic heart valve, shown with a side elevational view of the distal portion of a transfemoral catheter assembly.
Figure 3B:
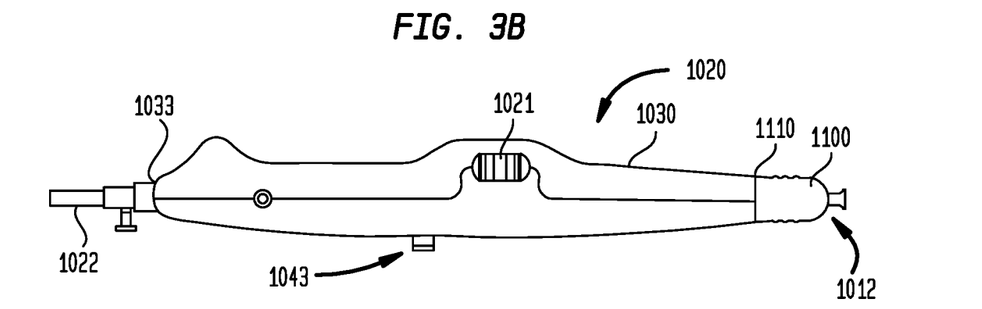
FIGS. 3B-D are side, bottom and top views of the operating handle of FIG. 3A.
Figure 3C:
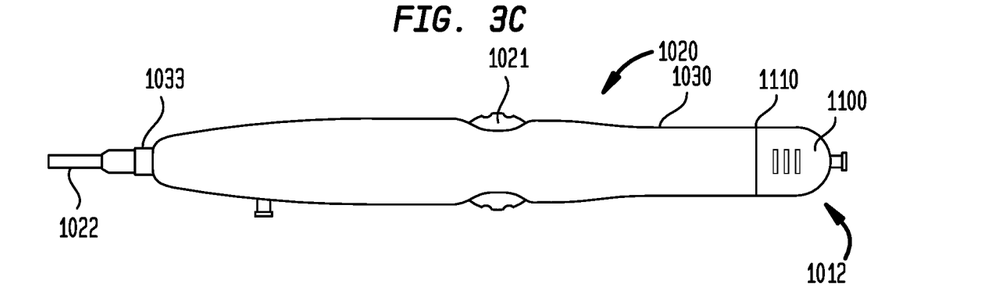
Figure 3D:
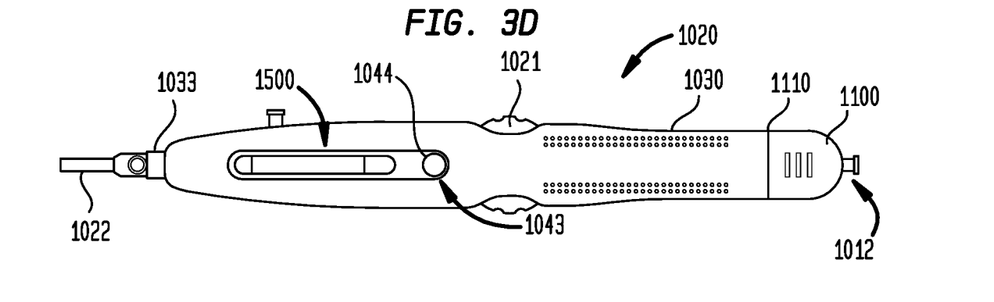

Optionally, handle 1020 further includes a resheathing lock 1043 adapted to prevent any movement of the carriage assembly within the frame 1030, thereby preventing a user from accidentally initiating deployment of a prosthetic valve (FIG. 3D). Resheathing lock 1043 may be coupled to main body 1041. The resheathing lock 1043 may include a laterally projecting pin 1044 which extends through an aperture in frame 1030. A spring 1045 may be assembled about pin 1044 and may be at least partially compressed between frame 1030 and an enlarged inner end of the pin so as to bias the pin to a position within frame 1030 in the unlocked position. As the user rotates deployment actuator 1021, outer shaft 1022 is pulled back and with it distal sheath 1024 to uncover a portion of compartment 1023. This process may continue until a predetermined position at which resheathing is no longer possible. When this predetermined position is reached, pin 1044 is pushed out through the aperture (FIG. 5A) until the pin protrudes from frame 1030, providing a visual indicator to the user that resheathing is no longer possible past this predetermined position. Further translation of the carriage assembly 1040 may be impeded until the user presses pin 1044 inwardly to confirm that further uncovering of compartment 1023 is desired (i.e., that the user wishes to fully deploy the prosthetic heart valve in its current position).

The initial distance that the carriage assembly 1040 can travel before actuating resheathing lock 1043 may depend on the structure of the particular prosthetic valve to be deployed. Preferably, the initial travel distance of the carriage assembly 1040 is about 3 mm to about 5 mm less than the crimped valve length (e.g., about 3 mm to 5 mm of the valve may remain covered to permit resheathing). Alternatively, the initial travel distance of the carriage assembly 1040 may be about 40 mm to about 45 mm, which is about 80% to about 90% of the length of an exemplary 50 mm valve. In other arrangements, the initial distance that the carriage assembly 1040 can travel can be determined as a percentage of the length of the prosthetic valve and/or of the compartment 1023, including, for example, 50%, 60%, 70%, 75%, 85%, or 95%. Thus, resheathing lock 1043 may allow uncovering of compartment 1023 up to a maximum distance or percentage, and allow further uncovering only after the user has pressed on laterally projecting pin 1044 to confirm that additional release (e.g., full release of the prosthetic heart valve) is desired.

A second technique, referred to as a "coarse technique," may be used to cover and uncover compartment 1023 more quickly and with less precision than the fine technique described above. Specifically, hub 1100 may be coupled to the proximal end of inner shaft 1026 and may be capable of moving the inner shaft relative to frame 1030 to facilitate opening and closing of the compartment 1023. This coarse movement may be used when no prosthetic heart valve is present in the compartment, such as, for example, when the compartment is to be opened prior to loading the prosthetic heart valve, and when the compartment is to be closed after the valve has been fully deployed. A mechanical lock 1110 may couple hub 1100 to frame 1030 to prevent accidental movement during use. For example, hub 1100 and a portion of frame 1030 may be threadedly engaged such that a rotation of the hub relative to the frame is required to release the hub from the frame. After lock 1110 has been disengaged, hub 1100 may be used to quickly cover or uncover the compartment. Movement of outer shaft 1022 with respect to inner shaft 1026 may open and close the compartment. Thus, pushing hub 1100 (and thus distal movement of inner shaft 1022) opens compartment 1023 and pulling hub 1100 closes the compartment.

Optionally, an indicator window 1500 (FIG. 6) may be disposed on top of frame 1030 and include a series of increments 1510 showing a percent or extent of deployment of the prosthetic heart valve. A scrolling bar 1520 may move along window 1500 past the series of increments 1510 as deployment continues to illustrate to the user the extent to which the prosthetic heart valve has been deployed. As illustrated, scrolling bar 1520 indicates that a prosthetic heart valve is approximately 37.5% deployed. Indicator window 1500 further includes a critical indicator 1530 showing the position past which resheathing is no longer possible. Resheathing lock 1043 may be activated as scrolling bar 1520, which is coupled to main body 1041 reaches position 1530.

The operation of the delivery device 1010 to deploy a prosthetic valve will now be described. Device 1010 may be shipped with outer shaft 1022 in its proximal-most position. Hub 1100 may also be initially shipped in a proximal-most position, the hub being spaced away from frame 1030. To load the delivery device 1010 with a collapsible prosthetic valve, a user can push hub 1100 (and advance inner shaft 1022) to expose the compartment 1023 (FIG. 7B), thread the inner shaft 1026 through the valve, couple the valve to the retainer 1025, and slide the distal sheath back over compartment to compress or crimp the valve by rotating deployment actuator 1021 (FIG. 7A), until the valve is fully covered in its compressed state by the distal sheath and the compartment is closed. In this starting condition, the handle 1020 will be in an initial state with the carriage assembly 1040 at its distalmost position within the frame 1030, the resheathing lock 1043 will be in an unlocked state with pin 1044 disposed within frame 1030, the hub 1100 in its distal-most position, and the deployment indicator will show 0% deployment.

To use the operating handle 1020 to deploy the prosthetic valve, the user can rotate the deployment actuator 1021 (FIG. 7A), causing the carriage assembly 1040 to slide proximally within the elongated space 1035 in frame 1030. Because the distal sheath 1024 is affixed to the outer shaft 1022, which in turn is affixed to the carriage assembly 1040, sliding the carriage assembly proximally relative to the frame will cause the distal sheath to move proximally. Since the inner shaft 1022 is at this point fixed to frame 1030, it will not move. Hence, the proximal movement of distal sheath 1024 relative to inner shaft 1022 will uncover the compartment 1023, thereby exposing and initiating deployment of the valve located therein.

Movement of the carriage assembly 1040 proximally may continue only until the resheathing lock 1043 is actuated and pin 1044 protrudes from frame 1030. At this point, the distal sheath 1024 will not be fully withdrawn from the compartment 1023, and the prosthetic valve will not be fully deployed. Moreover, indicator window 1500 will show that scrolling bar 1520 has reached critical indicator 1530 and that any further uncovering of the compartment will fully deploy the prosthetic heart valve and prevent its resheathing.

When the deployment procedure has reached this juncture, the user can evaluate the position of the valve and determine whether the annulus end of the valve is properly aligned relative to the patient's native valve annulus. If repositioning is desired, the user may resheathe the valve by using deployment actuator 1021 to slide the carriage assembly 1040 distally within the frame 1030, thereby moving the distal sheath 1024 distally over the compartment 1023 and over the partially deployed valve to recollapse the expanded portion of the valve. With the valve resheathed, the user can reposition the catheter assembly 1016 and commence the deployment procedure once again.

Once the valve has been properly positioned relative to the aortic annulus, the user may complete the deployment process. To do so, the user presses pin 1044 through the aperture in the frame, releasing lock 1043, which frees carriage assembly 1040 to continue its movement proximally within the frame 1030. The user can complete the deployment of the valve by continuing to slide the carriage assembly 1040 proximally, for example, by rotating the deployment actuator 1021. When the valve has been fully unsheathed, the stent portion of the valve self-expands and disengages from the retainer 1025, thereby releasing the valve from the catheter assembly 1016. Hub 1100 may once again be used to quickly cover the compartment and the delivery device may be removed from the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

In summary, the disclosure herein recites multiple embodiments to summarize the foregoing. Described herein is a delivery device for a collapsible prosthetic heart valve. The delivery device may include an inner shaft, a distal sheath disposed about a portion of the inner shaft and forming a compartment with the inner shaft, and a handle including a frame having a longitudinal axis, a proximal end and a distal end. The compartment may be adapted to receive the prosthetic heart valve, the inner shaft and the distal sheath being movable relative to one another. The handle may include a deployment actuator and a hub, each of the deployment actuator and the hub being independently capable of opening and closing the compartment. The handle may include a resheathing lock configured to alert a user of a position of the distal sheath and to impede movement of the distal sheath. The handle may include an indicator disposed on the frame and capable of showing an extent of deployment of the prosthetic heart valve; and/or the deployment actuator may include a wheel having an axis of rotation disposed transverse to the longitudinal axis of the frame; and/or the deployment actuator may be capable of longitudinally translating the distal sheath to cover or uncover the compartment; and/or the hub may be disposed adjacent the proximal end of the frame and may be capable of longitudinally translating the inner shaft to cover or uncover the compartment; and/or the delivery device may include a carriage assembly having a first gear, a second gear and a threaded rod, the first gear and the second gear being arranged to convert rotation of the deployment actuator into translation of the threaded rod along the longitudinal axis of the frame; and/or the delivery device may be configured and arranged for use in a transfemoral delivery approach; and/or the delivery device may be configured and arranged for use in a transapical delivery approach; and/or the resheathing lock may include a pin having a first position in which the pin is disposed within the frame, and a second position in which the pin protrudes from the frame; and/or the predetermined position may be a position at which the prosthetic heart valve has been partially deployed so that any further withdrawing of the distal sheath would result in the prosthetic heart valve being incapable of being resheathed.

Also described herein is another delivery device for a collapsible prosthetic heart valve. The delivery device may include an inner shaft, a distal sheath disposed about a portion of the inner shaft and forming a compartment with the inner shaft, and a handle including a frame having a longitudinal axis, a proximal end and a distal end. The compartment may be adapted to receive the prosthetic heart valve. The inner shaft and the distal sheath may be movable relative to one another. The handle may include a deployment actuator and a hub, each of the deployment actuator and the hub being independently capable of opening and closing the compartment; and/or the delivery device may include a resheathing lock configured to visually alert a user of a predetermined position of the outer shaft and to impede movement of the distal sheath; and/or the resheathing lock may include a pin having a first position in which the pin is disposed within the frame, and a second position in which the pin protrudes from the frame; and/or the resheathing lock may be configured to be pressed by the user to allow movement of the outer shaft; and/or the delivery device may include an indicator disposed on the frame and capable of showing an extent of deployment of the prosthetic heart valve; and/or the indicator may include a window in the frame having a series of increments, a critical indicator showing a position past which resheathing of the prosthetic heart valve is no longer possible, and a scrolling bar to illustrate the extent of deployment of the prosthetic heart valve.

Also described herein is yet another delivery device for a collapsible prosthetic heart valve. The delivery device may include an inner shaft, a distal sheath disposed about a portion of the inner shaft and forming a compartment with the inner shaft, and a handle including a frame having a longitudinal axis, a proximal end and a distal end. The compartment may be adapted to receive the prosthetic heart valve. The inner shaft and the distal sheath may be movable relative to one another. The handle may include a visual indicator disposed on the frame and capable of showing an extent of deployment of the prosthetic heart valve; and/or the indicator may include a window in the frame having a series of increments, a critical indicator showing a position past which resheathing of the prosthetic heart valve is no longer possible, and a scrolling bar to illustrate the extent of deployment of the prosthetic heart valve; and/or the delivery device may include a resheathing lock configured to alert a user of a predetermined position of the distal sheath and to impede movement of the distal sheath.

The invention claimed is:

1. A delivery device for a collapsible prosthetic heart valve, the delivery device comprising:
   an inner shaft;
   a distal sheath positionable about a portion of the inner shaft to cover a compartment formed around the inner shaft, the compartment being adapted to receive the prosthetic heart valve, the inner shaft and the distal sheath being movable relative to one another; and
   a handle including a frame having a longitudinal axis, a proximal end and a distal end, the handle further including a deployment actuator and a hub, each of the deployment actuator and the hub being movable and independently capable of positioning the distal sheath relative to the compartment such that the compartment is covered or uncovered, wherein the deployment actuator includes a wheel having an axis of rotation disposed transverse to the longitudinal axis of the frame.

2. The delivery device of claim 1, wherein the deployment actuator is capable of longitudinally translating the distal sheath to cover or uncover the compartment.

3. The delivery device of claim 1, wherein the hub is disposed adjacent the proximal end of the frame and is capable of longitudinally translating the inner shaft to cover or uncover the compartment.

4. The delivery device of claim 1, further including a carriage assembly having a first gear, a second gear and a threaded rod, the first gear and the second gear being arranged to convert rotation of the deployment actuator into translation of the threaded rod along the longitudinal axis of the frame.

5. The delivery device of claim 1, wherein the delivery device is configured and arranged for use in a transfemoral delivery approach.

6. The delivery device of claim 1, wherein the delivery device is configured and arranged for use in a transapical delivery approach.

7. The delivery device of claim 1, further comprising a resheathing lock configured to alert a user of a position of the distal sheath and to impede movement of the distal sheath, and an indicator disposed on the frame and capable of showing an extent of deployment of the prosthetic heart valve relative to the distal sheath.

8. The delivery device of claim 7, wherein the resheathing lock includes a pin having a first position in which the pin is disposed within the frame, and a second position in which the pin protrudes from the frame.

9. The delivery device of claim 8, wherein the position of the distal sheath is displayed on the indicator relative to a predetermined position at which the prosthetic heart valve has been partially deployed so that any further withdrawing of the distal sheath would result in the prosthetic heart valve being incapable of being resheathed.

10. A delivery device for a collapsible prosthetic heart valve, the delivery device comprising:
an inner shaft;
a distal sheath positionable about a portion of the inner shaft to cover a compartment formed around the inner shaft, the compartment being adapted to receive the prosthetic heart valve, the inner shaft and the distal sheath being movable relative to one another;
a handle including a frame having a longitudinal axis, a proximal end and a distal end, the handle further including a deployment actuator and a hub, each of the deployment actuator and the hub being movable and independently capable of positioning the distal sheath relative to the compartment such that the compartment is covered or uncovered;
a carriage assembly having a first gear, a second gear and a threaded rod, the first gear and the second gear being arranged to convert rotation of the deployment actuator into translation of the threaded rod along the longitudinal axis of the frame.

11. The delivery device of claim 10, further comprising a resheathing lock configured to visually alert a user of a predetermined position of the distal sheath and to impede movement of the distal sheath.

12. The delivery device of claim 11, wherein the resheathing lock includes a pin having a first position in which the pin is disposed within the frame, and a second position in which the pin protrudes from the frame.

13. The delivery device of claim 12, wherein the resheathing lock is configured to be pressed by the user to allow movement of the distal sheath.

14. The delivery device of claim 10, further comprising an indicator disposed on the frame and capable of showing an extent of deployment of the prosthetic heart valve relative to the distal sheath.

15. The delivery device of claim 14, wherein the indicator includes a window in the frame having a series of increments, a critical indicator showing a position past which resheathing of the prosthetic heart valve is no longer possible, and a scrolling bar to illustrate the extent of deployment of the prosthetic heart valve.

16. A delivery device for a collapsible prosthetic heart valve, the delivery device comprising:
an inner shaft;
a distal sheath positionable about a portion of the inner shaft to cover a compartment formed around the inner shaft, the compartment being adapted to receive the prosthetic heart valve, the inner shaft and the distal sheath being movable relative to one another; and
a handle including a frame having a longitudinal axis, a proximal end and a distal end, the handle further including a visual indicator disposed on the frame and capable of showing an extent of deployment of the prosthetic heart valve relative to the distal sheath,
wherein the visual indicator includes a window in the frame having a series of increments, a critical indicator showing a position past which resheathing of the prosthetic heart valve is no longer possible, and a scrolling bar to illustrate the extent of deployment of the prosthetic heart valve.

17. The delivery device of claim 16, further comprising a resheathing lock configured to alert a user of a predetermined position of the distal sheath and to impede movement of the distal sheath.

* * * * *